US00PP24453P2

(12) United States Plant Patent
Isobe et al.

(10) Patent No.: US PP24,453 P2
(45) Date of Patent: May 13, 2014

(54) ***PETUNIA* PLANT NAMED 'SUNSURFSIROU'**

(50) Latin Name: *Petunia×hybrida*
Varietal Denomination: Sunsurfsirou

(75) Inventors: Yasuko Isobe, Shiga (JP); Kenichi Suzuki, Osaka (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 148 days.

(21) Appl. No.: 13/506,497

(22) Filed: Apr. 23, 2012

(51) Int. Cl.
*A01H 5/00* (2006.01)

(52) U.S. Cl.
USPC ..... Plt./356.15

(58) Field of Classification Search
USPC ..... Plt./356.15, 356.1
See application file for complete search history.

*Primary Examiner* — June Hwu
(74) *Attorney, Agent, or Firm* — C. A. Whealy

(57) ABSTRACT

A new and distinct cultivar of *Petunia* plant named 'Sunsurfsirou', characterized by its mounding and trailing plant habit; vigorous growth habit; early flowering habit; long flowering period; large white-colored flowers with light yellow green-colored venation; and good garden performance.

1 Drawing Sheet

Botanical designation: *Petunia×hybrida.*
Cultivar denomination: 'SUNSURFSIROU'.

BACKGROUND OF THE INVENTION

The present invention relates to a new and distinct cultivar of *Petunia* plant, botanically known as *Petunia×hybrida* and hereinafter referred to by the name 'Sunsurfsirou'.

The new *Petunia* plant is a product of a planned breeding program conducted by the Inventors in Higashiomi, Shiga, Japan. The objective of the breeding program is to create new *Petunia* plants with trailing habit and attractive flower coloration.

The new *Petunia* plant is a naturally-occurring whole plant mutation of a proprietary selection of *Petunia×hybrida* identified as code name SB-W, not patented. The new *Petunia* plant was discovered and selected by the Inventors as a single flowering plant from within a population of plants of the mutation parent selection in a controlled environment in Higashiomi, Shiga, Japan in October, 2006.

Asexual reproduction of the new *Petunia* plant by terminal cuttings in a controlled environment in Higashiomi, Shiga, Japan since October, 2006 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurfsirou'. These characteristics in combination distinguish 'Sunsurfsirou' as a new and distinct *Petunia* plant:

1. Mounding and trailing plant habit.
2. Vigorous growth habit.
3. Early flowering habit.

4. Long flowering period.
5. Large white-colored flowers with light yellow green-colored venation.
6. Good garden performance.

Plants of the new *Petunia* can be compared to plants of the mutation parent selection. Plants of the new *Petunia* differ primarily from plants of the mutation parent selection in flower color as plants of the mutation parent selection have white-colored flowers with dull red purple-colored venation. In addition, plants of the new *Petunia* are more compact than plants of the mutation parent selection.

Plants of the new *Petunia* can also be compared to plants of the *Petunia* 'Sunsurfhowa', not patented. In side-by-side comparisons conducted in Higashiomi, Shiga, Japan, plants of the new *Petunia* and 'Sunsurfhowa' differed primarily in the following characteristics:

1. Plants of the new *Petunia* were broader and had longer internodes than plants of 'Sunsurfhowa'.
2. Leaf margins of plants of the new *Petunia* were more undulate than leaf margins of plants of 'Sunsurfhowa'.
3. Plants of the new *Petunia* and 'Sunsurfhowa' differed in flower throat color as plants of 'Sunsurfhowa' had pale yellow green-colored flower throats with yellow green-colored venation.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurfsirou' grown in a container.

The photograph at the bottom of the sheet is a close-up view of a typical flowering plant of 'Sunsurfsirou'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Sunsurfsirou'.

Parentage: Naturally-occurring whole plant mutation of a proprietary selection of *Petunia×hybrida* identified as code name SB-W, not patented.

Propagation:

*Type.*—By terminal cuttings.

*Time to initiate roots.*—About one week at temperatures of 15° C. to 20° C.

*Time to produce a rooted young plant.*—About three weeks at temperatures of 15° C. to 20° C.

*Root description.*—Fibrous; white in color.

*Rooting habit.*—Freely branching.

Plant description:

*Plant and growth habit.*—Mounding and trailing plant habit; moderately branching habit with numerous lateral branches developing per plant; pinching enhances lateral branch development; vigorous growth habit.

*Plant height.*—About 13.3 cm.

*Plant diameter.*—About 71.3 cm.

Lateral branch description:

*Length.*—About 52.3 cm.

*Diameter.*—About 3 mm.

*Internode length.*—About 4.6 cm.

*Strength.*—Strong, flexible.

*Aspect.*—Upright to decumbent.

*Texture.*—Pubescent.

*Color.*—Close to 143B.

Foliage description:

*Arrangement.*—Alternate, simple.

*Length.*—About 5.2 cm.

*Width.*—About 3 cm.

*Shape.*—Elliptic.

*Apex.*—Obtuse.

*Base.*—Attenuate.

*Margin.*—Entire, undulate.

*Texture, upper and lower surfaces.*—Pubescent.

*Venation pattern.*—Pinnate; reticulate.

*Color.*—Developing leaves, upper surface: Close to 143A. Developing leaves, lower surface: Close to 143B. Fully expanded leaves, upper surface: Close to 138A; venation, close to 143B. Fully expanded leaves, lower surface: Close to 143C; venation, close to 143C.

*Petioles.*—Length: About 9.1 mm. Diameter: About 1.8 mm. Texture, upper and lower surfaces: Pubescent. Color, upper and lower surfaces: Close to 144A.

Flower description:

*Flower arrangement and habit.*—Single salverform flowers arising from upper leaf axils; moderately freely flowering habit with usually about 17 flowers developing per plant; flowers face upright to outwardly.

*Fragrance.*—None detected.

*Natural flowering season.*—Early flowering habit, plants of the new *Petunia* initiate and develop flowers about three to four weeks after planting; long flowering period; flowering commences naturally during the spring and plants flower continuously throughout the summer until late autumn in Japan.

*Flower longevity.*—Individual flowers last about seven to ten days on the plant; flowers not persistent.

*Flower diameter.*—About 6 cm.

*Flower length (depth).*—About 5.4 cm.

*Throat diameter.*—About 1.4 cm.

*Tube diameter, base.*—About 3.7 mm.

*Tube length.*—About 2.9 cm.

*Flower buds.*—Shape: Cylindrical. Length: About 4.3 cm. Diameter: About 1.3 cm. Color: Close to 145C; venation, close to 145A.

*Corolla.*—Arrangement: Five petals fused at the base and opening into a flared trumpet. Petal length from throat: About 2.1 cm. Petal width: About 2.8 cm. Petal shape: Spatulate. Petal apex: Mucronate. Petal margin: Entire, week to moderate undulation. Petal texture, upper and lower surfaces: Smooth, glabrous. Throat texture: Smooth, glabrous. Tube texture: Pubescent. Color: Petal, when opening, upper and lower surfaces: Close to NN155C. Petal, fully opened, upper surface: Close to NN155C; venation, close to 150C. Petal, fully opened, lower surface: Close to NN155C; venation, close to 145B. Throat: Close to NN155C; venation, close to 199B. Tube: Close to NN155C; venation, close to 145B.

*Calyx.*—Arrangement: One star-shaped calyx tube with five sepals fused at the base per flower. Sepal length: About 2.1 cm. Sepal width: About 7.2 mm. Sepal shape: Narrowly elliptic. Sepal apex: Obtuse. Sepal margin: Entire, undulate. Sepal texture, upper and lower surfaces: Pubescent. Color: Developing sepals, upper surface: Close to 138A. Developing sepals, lower surface: Close to 138B. Fully developed sepals, upper surface: Close to 138A.

*Peduncles.*—Length: About 2.9 cm. Diameter: About 1.4 mm. Strength: Strong. Texture: Pubescent. Color: Close to 144B.

*Reproductive organs.*—Stamens: Quantity per flower: Five. Stamen length: About 1.4 cm to 1.9 cm. Anther shape: Ellipsoidal. Anther size: About 1.8 mm by 2.5 mm. Anther color: Close to 157A. Pollen amount: Abundant. Pollen color: Close to 158B. Pistils: Quantity per flower: One. Pistil length: About 1.9 cm. Style color: Close to 142C. Stigma shape: Transversely ellipsoidal. Stigma color: Close to 141C; mid-section, close to 141B. Ovary color: Close to 145A. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurfsirou' as illustrated and described.

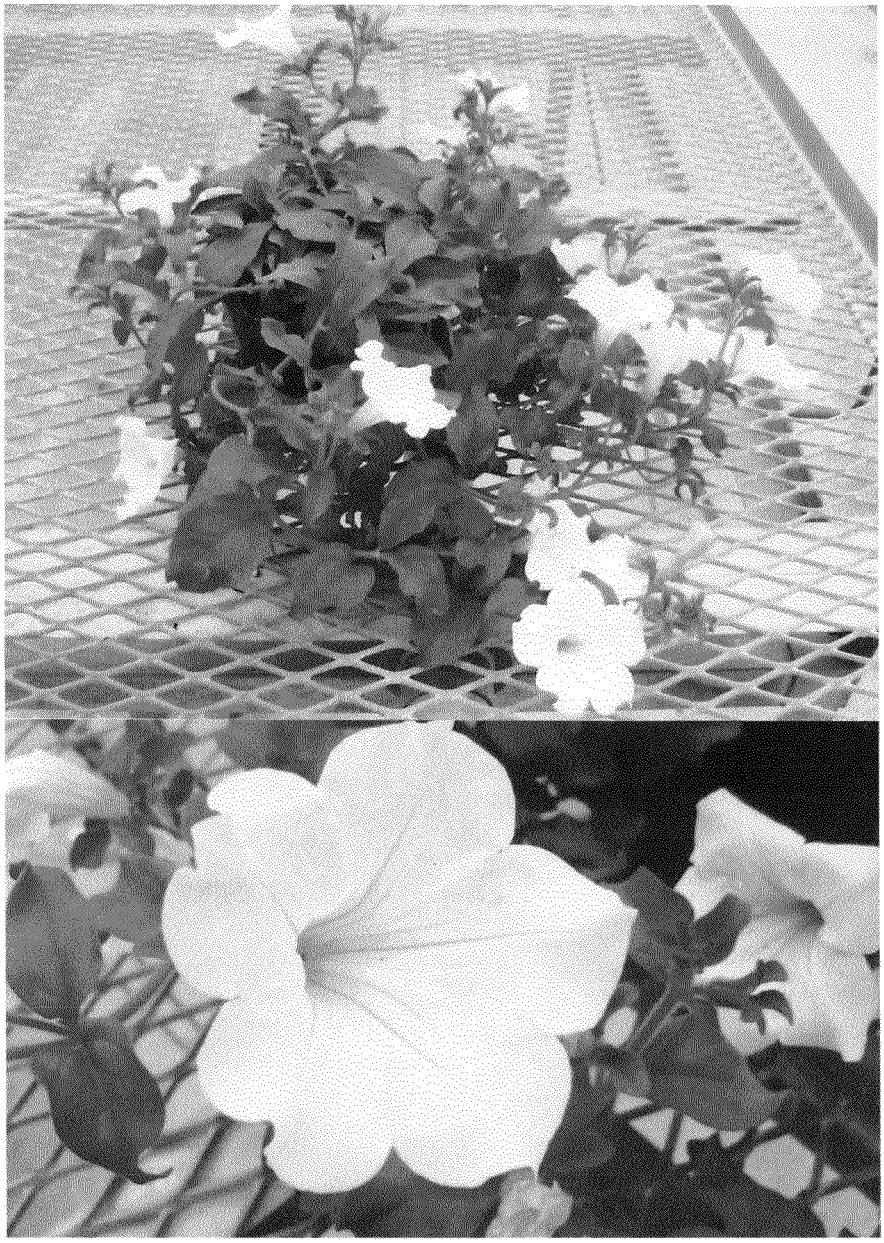

* * * * *